(12) United States Patent
Fetzer et al.

(10) Patent No.: US 8,336,384 B2
(45) Date of Patent: Dec. 25, 2012

(54) ULTRASONIC PROBE

(75) Inventors: Barry A. Fetzer, Renton, WA (US);
James C. Kennedy, Renton, WA (US);
Thomas E. Riechers, Bonney Lake, WA (US); Fred D Young, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 303 days.

(21) Appl. No.: 12/626,859

(22) Filed: Nov. 27, 2009

(65) Prior Publication Data
US 2010/0064812 A1 Mar. 18, 2010

Related U.S. Application Data

(63) Continuation-in-part of application No. 11/345,904, filed on Feb. 2, 2006, now Pat. No. 7,637,163, and a continuation-in-part of application No. 11/345,905, filed on Feb. 2, 2006.

(51) Int. Cl.
*G01N 29/28* (2006.01)
*G01N 29/24* (2006.01)

(52) U.S. Cl. .......................... 73/644; 73/636

(58) Field of Classification Search .......... 73/636, 73/644
See application file for complete search history.

(56) References Cited

U.S. PATENT DOCUMENTS

| | | | | |
|---|---|---|---|---|
| 2,992,553 | A | | 7/1961 | Joy |
| 3,616,684 | A | * | 11/1971 | Nusbickel, Jr. ................ 73/635 |
| 5,814,731 | A | * | 9/1998 | Alexander et al. ............. 73/644 |
| 6,298,727 | B1 | * | 10/2001 | Fleming et al. ................ 73/644 |
| 7,284,434 | B1 | * | 10/2007 | Fleming ........................ 73/644 |
| 7,571,649 | B2 | * | 8/2009 | Young ........................... 73/644 |
| 2005/0126293 | A1 | * | 6/2005 | Dasch ........................... 73/618 |

* cited by examiner

*Primary Examiner* — Daniel Larkin
*Assistant Examiner* — Rose M Miller

(57) ABSTRACT

An ultrasonic probe includes a probe body having a contact surface and a cavity that is open at the contact surface, an ultrasonic transducer carried by the body, and a spacer within the cavity. The spacer has a first surface acoustically coupled to the transducer, and a second (coupling) surface within the cavity. The spacer propagates an acoustic signal between the transducer and the coupling surface. The coupling surface is spaced apart from the contact surface to form a recess within the body. The body further has at least one port for circulating a coupling fluid into the recess. Depth of the recess is selected to balance gravitational force on the coupling fluid versus surface tension of the coupling fluid so a bead of the fluid forms over an edge of a structure under inspection as the probe is moved over the edge.

19 Claims, 4 Drawing Sheets

ULTRASONIC PROBE

BACKGROUND

Nondestructive inspection (NDI) of a structure involves thoroughly examining the structure without harming it or significantly disassembling it. Nondestructive inspection is commonly used in the aircraft industry to validate the health (e.g., integrity and fitness) of aircraft structures.

An ultrasonic probe may be used to perform NDI of a structure. A conventional probe typically includes a transducer having an array of elements that direct acoustic signals toward the structure and measure reflections of the signals.

An acoustic coupling fluid is used to propagate the acoustic signals between the probe and a structure under inspection. During inspection, a surface of the structure may be wetted with an acoustic coupling fluid such as water.

Edge related problems are experienced by an array losing coupling off the edge of a structure under inspection. As a probe is moved off the edge, the particular array element that is located off the structure's edge will lose coupling. If coupling between the probe and the structure is lost, acoustic signals will not be propagated from and to that array element. Consequently, reflected signals will not identify edges of the structure under inspection.

It would be desirable to maintain coupling over edges of structures during NDI with an ultrasonic probe.

SUMMARY

According to an embodiment herein, an ultrasonic probe includes a probe body having a contact surface and a cavity that is open at the contact surface, an ultrasonic transducer carried by the body, and a spacer within the cavity. The spacer has a first surface acoustically coupled to the transducer, and a second (coupling) surface within the cavity. The spacer propagates an acoustic signal between the transducer and the coupling surface.

The coupling surface is spaced apart from the contact surface to form a recess within the body. The body further has at least one port for circulating a coupling fluid into the recess. Depth of the recess is selected to balance gravitational force on the coupling fluid versus surface tension of the coupling fluid so a bead of the fluid forms over an edge of a structure under inspection as the probe is moved over the edge.

According to another embodiment herein, an ultrasonic probe includes a probe body having a contact surface and a cavity that is open at the contact surface, an ultrasonic transducer carried by the body, and a spacer within the cavity. The spacer includes a flexible diaphragm that provides a coupling surface within the cavity. The spacer propagates acoustic signals between the transducer and the coupling surface. The coupling surface is spaced apart from the contact surface to form a recess within the body. Pressure variations in the cavity can be created to cause the diaphragm to flex.

The probe body further has at least one port for circulating a coupling fluid into the recess. Depth of the recess is selected to balance gravitational force on the coupling fluid versus surface tension of the coupling fluid so a bead of the fluid forms over an edge of a structure under inspection as the probe is moved over the edge.

According to another embodiment herein, a system comprises an ultrasonic probe including a probe body having a contact surface and a cavity that is open at the contact surface, an ultrasonic transducer carried by the body, and a spacer within the cavity. The spacer has a first surface acoustically coupled to the transducer, and a second (coupling) surface within the cavity. The spacer propagates an acoustic signal between the transducer and the coupling surface. The coupling surface is spaced apart from the contact surface to form a recess within the body. Depth of the recess is selected to allow a bead of coupling fluid to form over an edge of a structure under inspection as the probe is moved over the edge.

The system further comprises a controller for creating C-scan presentations from signals detected by the transducer. The C-scan presentations identify edges in the structure under inspection.

DETAILED DESCRIPTION

Figure 1:
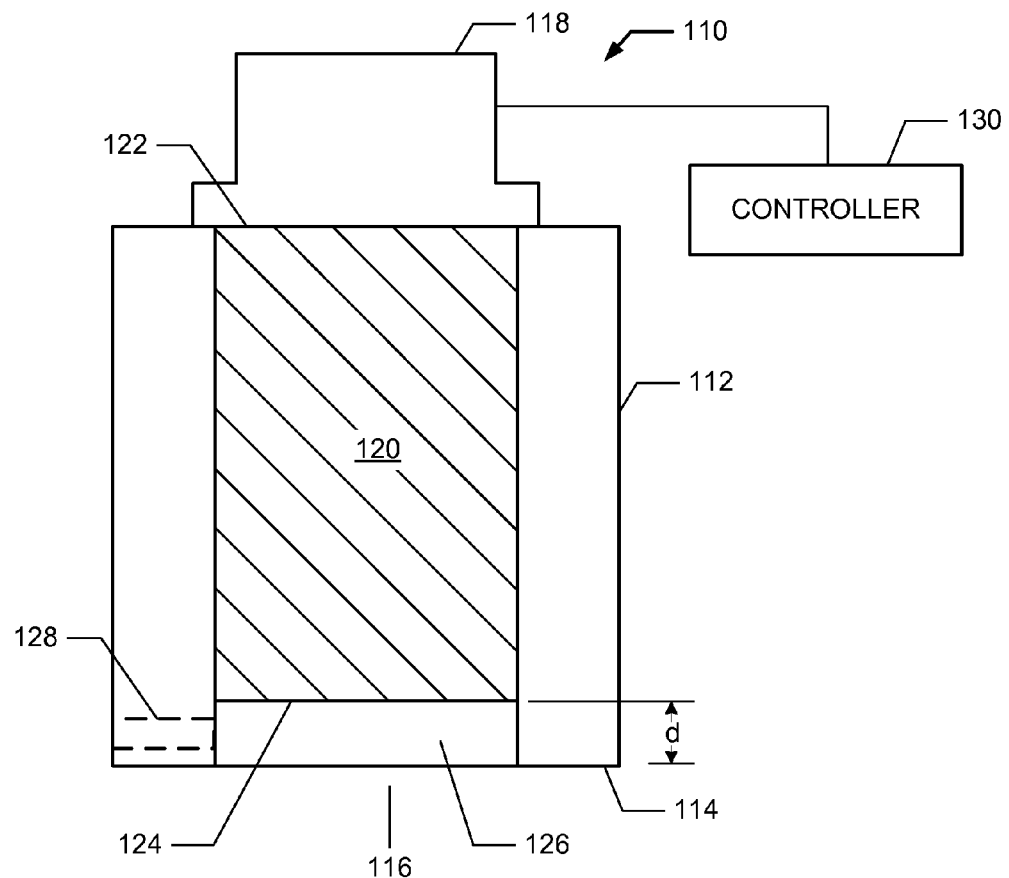
FIG. 1 is an illustration of an ultrasonic probe

Reference is made to FIG. 1, which illustrates an ultrasonic probe 110. The probe 110 includes a probe body 112 having a contact surface 114 at a first end of the probe body 112. The probe body 112 also has a cavity (e.g., a bore) 116 that is open at the contact surface 114. The probe body 112 may be made of a rigid material having a low coefficient of friction so as to slide easily. The probe body 112 does not propagate an acoustic signal along a structure under inspection.

An ultrasonic transducer 118 is carried by the probe body 112. The transducer 118 includes an array of elements. The array may comprise multiple crystals or a singular crystal that is sliced up into multiple elements. Ultrasonic defines the spectrum of frequency at which the array crystals oscillate.

The probe 110 further includes a spacer 120 within the cavity 116. The spacer 120 has a first surface 122 acoustically coupled to the transducer 118. The spacer 120 has a second surface 124 within the cavity 116. The second surface 124 is spaced apart from the contact surface 114 by a distance d.

The spacer 120 is used to propagate acoustic signals between the transducer 118 and the second surface 124. The second surface 124, in turn, is acoustically coupled to a structure under inspection. Hence, the second surface 124 will hereinafter be referred to as a "coupling" surface 124.

The probe body 112 has a volume 126 between the coupling surface 124 and the first end of the probe body 112. This volume 126 will hereinafter be referred to as a "recess" 126. The recess 126 has a depth d.

The probe body 112 further has at least one port 128 for circulating a coupling fluid into the recess 126. The coupling fluid will acoustically couple the coupling surface to the structure under inspection.

Figure 2A:
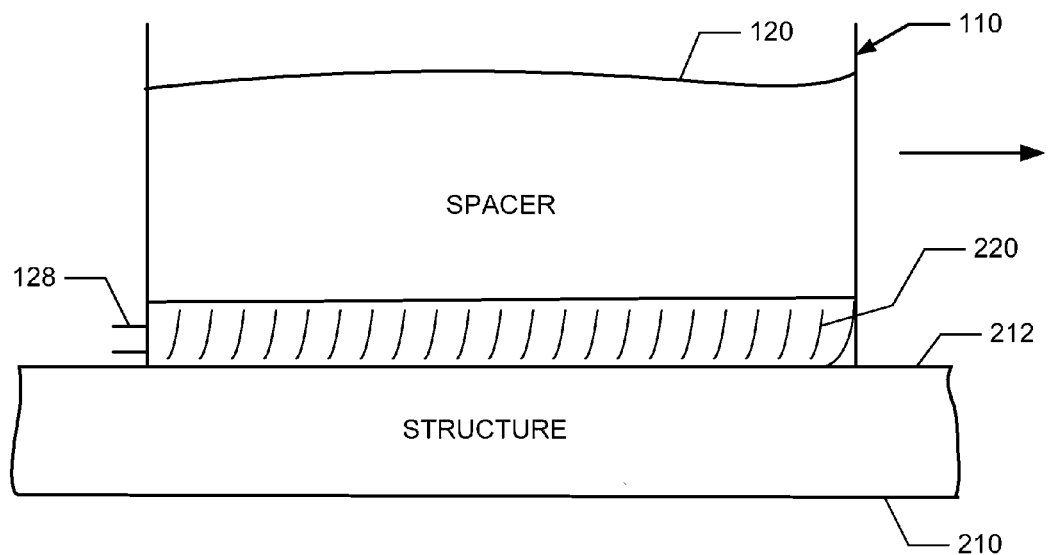
FIGS. 2*a*, 2*b* and 2*c* are illustrations of coupling fluid within a recess of the probe during inspection of a structure.

Additional reference is made to FIG. 2*a*, which illustrates the probe 110 and a structure 210 under inspection. During inspection of the structure 210, the contact surface 114 of the probe 110 is placed against a front surface 212 of the structure 210, and coupling fluid is circulated through the port 128 and into the recess 126. The coupling fluid acoustically couples the structure 210 to the coupling surface 124 of the spacer 120. Resulting is a film 220 of coupling fluid between the spacer 120 and structure 210.

The probe 110 is moved along the front surface 212 of the structure 210 (e.g., in the direction of the arrow). The coupling fluid adheres to both the spacer 120 and the structure 210 due to surface adhesion. The coupling film 220 is also elongated at the end of the spacer 120 due to surface tension.

As the probe 110 is moved along the structure 210, some of the coupling fluid will remain on the front surface 212 and, therefore, will be removed from the recess 126. That fluid will be replaced by new fluid entering from the port 128.

The transducer 118 is operated in pulse echo ("PE") mode to generate sound pulses that are transmitted to the front surface of the structure 210, and measure reflected acoustic energy. Some of the acoustic energy will reflect off the front surface 212, some will reflect off a back surface of the structure 210, and some energy will reflect off any irregularities (e.g., voids, delaminations) between the front and back surfaces.

A controller 130 processes the reflected signals. In some embodiments, the controller 130 processes the reflected signals into two electronic domains of amplitude and time response. These two domains of amplitude and time response can be further processed. These domains can be sent to a computer for additional processing or they can be additionally processed by the controller 130. The additional processing may include generating presentations of the returned signals. C-scan presentations, for example, display amplitude or time response relative to physical X and Y dimensional coordinates. The C-scan presentation most clearly illustrates the edges of a structure under inspection.

The controller 130 may have multiple time gates. A time gate refers to a window of analysis in time and amplitude. Gates are typically used to filter out data from front surfaces, etc. A time gate for pulse echo is usually set to find reflections within the structure 110, or it could be adjusted to look at a specific part of the reflection to determine whether an irregularity is at one particular depth. It is common practice to gate beyond the 120 delay line.

Figure 2B:
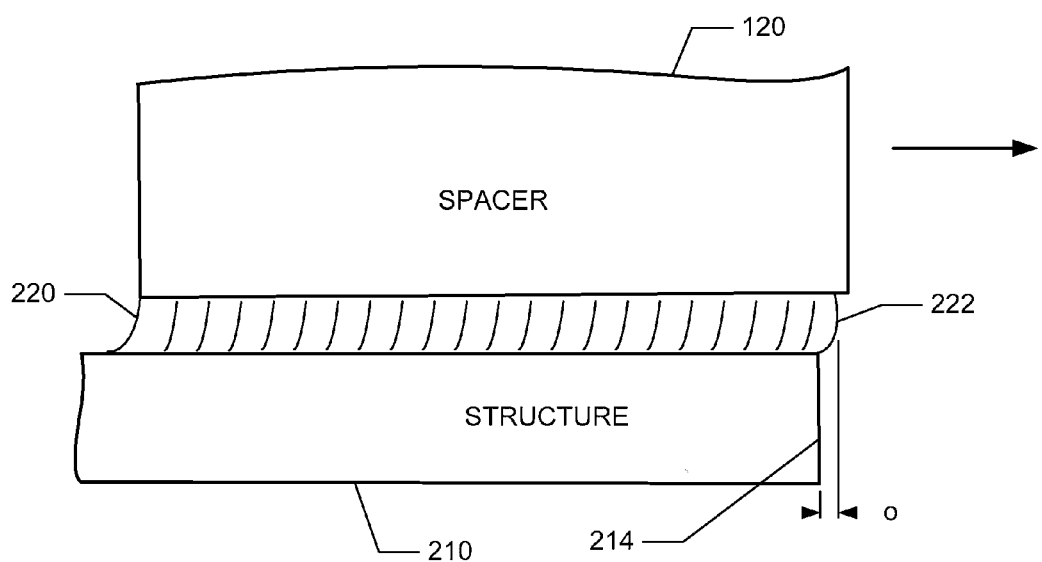

Additional reference is made to FIG. 2b (the probe body has been omitted for clarity). As the probe 110 is moved over an edge 214 of the structure 210, a bead 222 of coupling fluid is formed over the edge 214. The bead 222 is formed due to surface tension, which is a function of the cohesive force between molecules of the coupling fluid 220. Due to this surface tension, the bead 222 of the coupling fluid remains coupled over the edge 214 of the structure 210.

The depth d determines the height of the coupling fluid. Excessive height negates the surface tension. The surface tension is a factor of fluid height or recess depth d. If the recess is too deep, gravity will be too strong of a proponent to the surface tension, whereby the fluid will not remain coupled at the edge 214 of the structure 210. Thus, the depth d of the recess 126 is selected to balance gravitational force on the coupling fluid versus surface tension of the coupling fluid so a bead of the fluid forms over the edge 214 of the structure 210 under inspection as the probe 110 is moved over the edge 214. The distance that the bead hangs over the edge 214 (the "overhang") is referenced by letter "o."

Figure 2C:
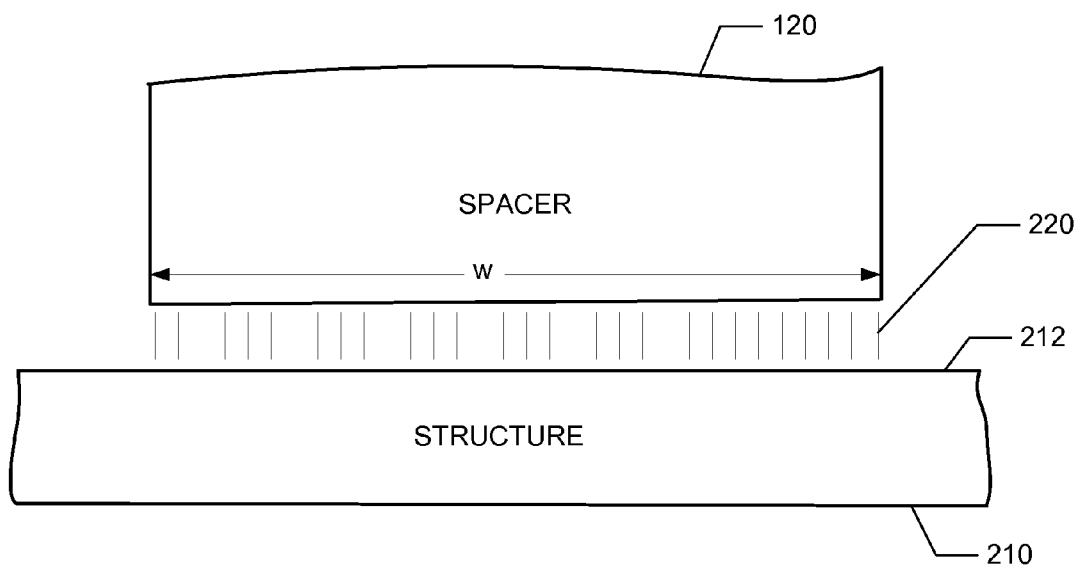

Additional reference is made to FIG. 2c. The bead 222 spans the width w of the recess 126.

A probe was constructed, and various recess depths were tested. For a coupling fluid such as water, the depth d of the recess 126 may be in the range of 0.010 inches to 0.040 inches. In one instance, water was supplied to the recess at a rate of 0.250 fl oz/sec. Depth d of the recess was 0.020 inches, and width w was 0.525 inches. Overhang o of the water bead was measured at 0.075 inches, and increased to 0.090 inches before running off onto the edge 214 of the structure 210.

In another instance, recess depth d was increased to 0.35 inches. Overhang (o) of the bead was reduced to 0.035 inches.

In yet another instance, recess depth d was increased to 0.040 inches. At that depth, the water bead started to disappear. Thus, increasing the recess to a depth of roughly 0.040" stopped the water bead from forming.

Figure 3:
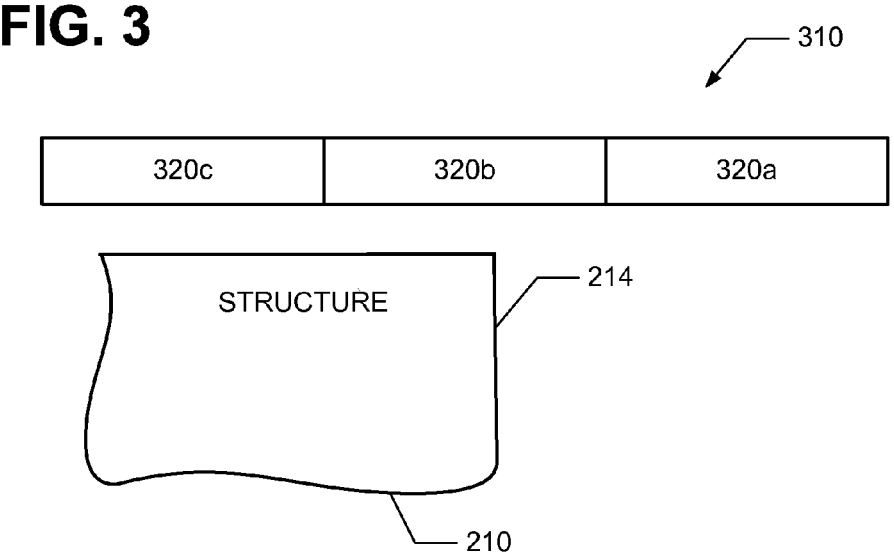
FIG. 3 is an illustration of elements of a transducer array with respect to an edge of a structure under inspection.

The advantage of the bead 222 is made clear by reference to FIG. 3. FIG. 3 illustrates an array 310 having multiple elements that are 0.050" apart. A first element 320a of the array 310 is off an edge 214 of the structure 210 under inspection, a second element 320b is over the edge 214, and a third element 320c is 0.050 inches away from the edge 214, but still over the structure 210. These elements 320a-320c are butted together side by side. Without proper coupling, all three elements 320a-320c would lose data and no signals would be propagated into the structure 210. With some coupling, the third element 320c might provide some data. With good water coupling at the edge 214, the second and third elements 320b and 320c will provide solid signals. The first element 320a might even show some signal.

Edge definition would be affected by the right selection of frequency in terms of resolution. For instance, a 5 MHz frequency can be obtained by using a 1 mm pitch element and a 3 MHz frequency can be obtained by using a 1.5 mm pitch element. Since pitch is directly related to resolution, the higher frequency will result in finer resolution of the structure.

The probe 110 provides greater accuracy in testing, since signals at the edge are propagated. Consequently, more accurate presentations can be prepared.

Feeding fluid to a recess removes the need for external means to wet the surface with coupling fluid. Coupling the probe to a structure under inspection can be very difficult depending on the structure and the speed of inspection.

The probe 110 may have a connection to a gantry, robot or other scanning mechanism. The probe 110 may further include means (not shown) for recording position of the transducer array during inspection. For example, the means could include an encoder. Position of the transducer array is used in presentations such as C-scans.

Water is the preferred coupling fluid. However, a coupling fluid herein is not limited to water. For a coupling fluid having a different surface tension, the recess depth might be different.

A spacer herein is not limited to any particular type. As a first example, the spacer is made of a solid or semi-solid material as disclosed in assignee's U.S. Ser. No. 11/345,904 (now U.S. Pat. No. 7,637,163), which is incorporated herein by reference.

As a second example, the spacer includes a flexible diaphragm as disclosed in assignee's copending U.S. Ser. No. 11/345,905, which is also incorporated herein by reference. The flexible diaphragm is within the probe body, but is offset from the contact surface by a nominal distance d. The flexible diaphragm provides the coupling surface. A chamber is formed by the diaphragm, the probe body and the transducer. Pressure in the chamber can be varied to cause the diaphragm to flex inwardly and outwardly.

In some embodiments, the chamber contains a delay fluid. Chamber pressure is controlled by controlling flow rate of the delay fluid. A fluid circuit and controller can be used to control the flow rate of the delay fluid.

Figure 4A:
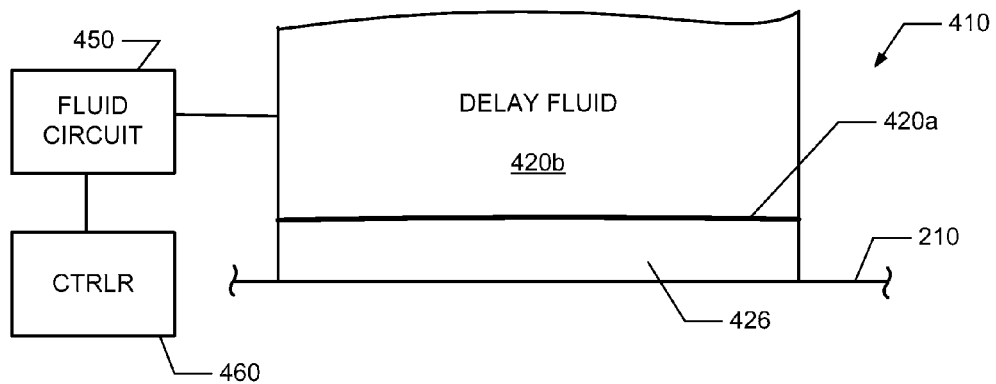
FIGS. 4*a*-4*c* are illustrations of a probe having a flexible diaphragm.
Figure 4B:
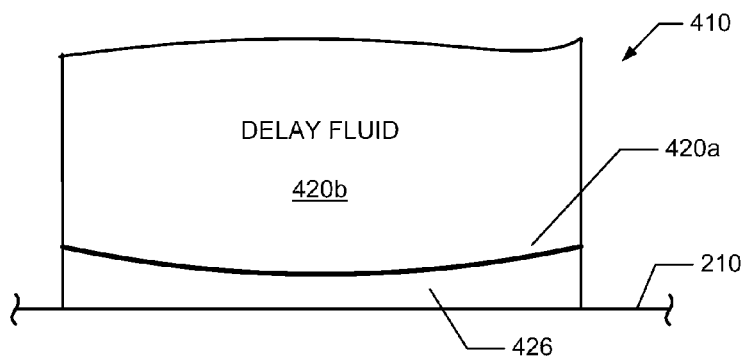
Figure 4C:
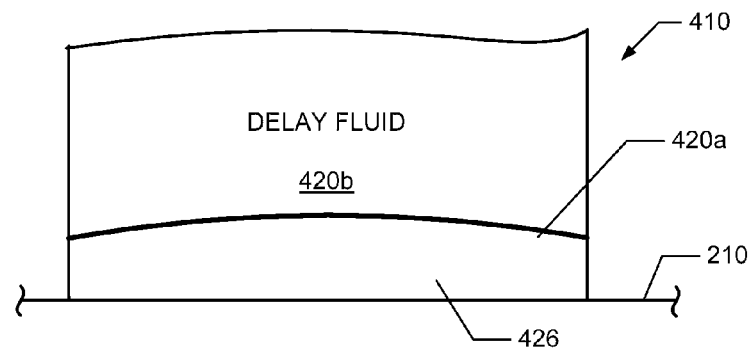

Reference is now made to FIGS. 4a-4c, which illustrate a probe 410 having a probe body and a spacer including a flexible diaphragm 420a, and a chamber filled with delay fluid 420b. A chamber inlet and outlet (not shown) allow the delay fluid 420b to circulate through the chamber. A fluid circuit 450 and controller 460 are used to control the flow rate of the delay fluid 420*b* through the chamber. FIG. 4*a* shows the flexible diaphragm 420*a* unflexed, FIG. 4*b* shows the diaphragm 420*a* flexed outward, and FIG. 4*c* shows the diaphragm 420*a* flexed inward.

The flexible diaphragm 420*b* can be actively flexed in response to the probe 410 encountering surface discontinuities such as protrusions and depressions. The diaphragm 420*b* can be flexed inwardly to a concave position so the probe 410 can better accommodate surface protrusions. The diaphragm 420*b* can be flexed outwardly to a convex position so the probe can better accommodate surface depressions. Thus, by flexing the diaphragm 420*b*, the layer of coupling fluid in the recess 426 can be maintained at a relatively constant thickness. As a result, coupling can be better maintained over surface discontinuities. The flexible diaphragm 420*b* can also be flexed to avoid slight curvatures in the structure 210 under inspection, which might otherwise cause the probe 410 to rock and lose coupling.

Figure 5:
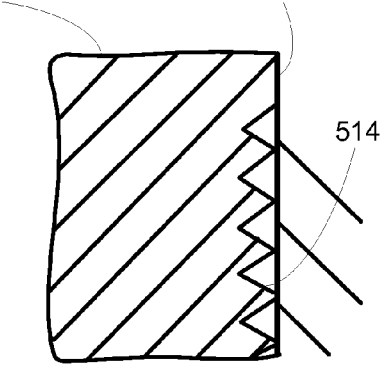
FIG. 5 is an illustration of grooves in a cavity wall of a probe body.

The probe body is not limited to a cavity having smooth walls. In some embodiments, grooves 514 are formed in the cavity walls 512 of a probe body 510 (see FIG. 5). The grooves absorb stray signals incident upon the cavity walls and thereby minimize the amount of stray signals that are returned to the transducer. This feature is also disclosed in U.S. Ser. No. 11/345,904.

The invention claimed is:

1. An ultrasonic probe comprising:
   a probe body having a contact surface and a cavity that is open at the contact surface;
   an ultrasonic transducer carried by the body; and
   a spacer within the cavity, the spacer having a first surface acoustically coupled to the transducer, and a second surface within the cavity, the spacer for propagating an acoustic signal between the transducer and the second surface, the second surface spaced apart from the contact surface to form a recess within the body;
   the body further having at least one port for circulating a coupling fluid into the recess;
   wherein depth of the recess is selected to balance gravitational force on the coupling fluid versus surface tension of the coupling fluid so a bead of the fluid forms over an edge of a structure under inspection as the probe is moved over the edge.

2. The probe of claim 1, wherein the depth for coupling fluid is in the range of 0.010 inches to 0.040 inches.

3. The probe of claim 2, wherein the depth is about 0.020 inches for water.

4. The probe of claim 1, wherein the spacer includes a flexible diaphragm forming the second surface, and a delay fluid between the diaphragm and the transducer.

5. The probe of claim 4, further comprising means for controlling flow rate of the delay fluid to actively flex the diaphragm.

6. The probe of claim 1, wherein the spacer includes one of a solid and semi-solid material.

7. The probe of claim 1, wherein walls of the cavity have grooves for absorbing stray acoustic signals.

8. An ultrasonic probe comprising:
   a probe body having a contact surface and a cavity that is open at the contact surface;
   an ultrasonic transducer carried by the body; and
   a spacer within the cavity, the spacer including a flexible diaphragm for providing a coupling surface within the cavity, the spacer for propagating acoustic signals between the transducer and the coupling surface, the coupling surface spaced apart from the contact surface to form a recess within the body, pressure variations in the cavity causing the diaphragm to flex;
   the body further having at least one port for circulating a coupling fluid into the recess;
   wherein depth of the recess is selected to balance gravitational force on the coupling fluid versus surface tension of the coupling fluid so a bead of the fluid forms over an edge of a structure under inspection as the probe is moved over the edge.

9. The probe of claim 8, wherein the recess depth is in the range of 0.010 inches to 0.040 inches.

10. The probe of claim 8, wherein the recess depth is about 0.020 inches.

11. The probe of claim 8, further comprising means for controlling flow rate of delay fluid in the cavity to actively flex the diaphragm.

12. The probe of claim 8, wherein walls of the cavity have grooves for absorbing stray acoustic signals.

13. A system comprising:
   an ultrasonic probe including a probe body having a contact surface and a cavity that is open at the contact surface, an ultrasonic transducer carried by the body, and a spacer within the cavity, the spacer having a first surface acoustically coupled to the transducer, and a second surface within the cavity, the spacer for propagating an acoustic signal between the transducer and the second surface, the second surface spaced apart from the contact surface to form a recess within the body, wherein depth of the recess is selected to allow a bead of coupling fluid to form over an edge of a structure under inspection as the probe is moved over the edge; and
   a controller for creating C-scan presentations from signals detected by the transducer, the C-scan presentations identifying edges in the structure under inspection.

14. The system of claim 13, wherein the depth for coupling fluid is in the range of 0.010 inches to 0.040 inches.

15. The system of claim 14, wherein the depth is about 0.020 inches for water.

16. The system of claim 13, wherein the spacer includes a flexible diaphragm forming the second surface; and a delay fluid between the diaphragm and the transducer.

17. The system of claim 16, further comprising means for controlling flow rate of the delay fluid to actively flex the diaphragm.

18. The system of claim 13, wherein the spacer includes one of a solid and semi-solid material.

19. The system of claim 13, wherein walls of the cavity have grooves for absorbing stray acoustic signals.

* * * * *